United States Patent [19]

Feldstein et al.

[11] 4,378,813

[45] Apr. 5, 1983

[54] SYSTEM AND METHOD FOR MOVING A PROBE TO FOLLOW MOVEMENTS OF TISSUE

[76] Inventors: Alan M. Lovelace, Administrator of the National Aeronautics and Space Administration, with respect to an invention of Cyril Feldstein, late of Sierra Madre, Calif.; Thomas W. Andrews, Pasadena, Calif.; Donald W. Crawford; Mark A. Cole, both of Long Beach, Calif.

[21] Appl. No.: 263,957

[22] Filed: May 15, 1981

[51] Int. Cl.³ .............................................. A61B 5/10
[52] U.S. Cl. .................................... 128/774; 128/782; 128/303 B
[58] Field of Search .............. 128/774, 782, 784, 635, 128/642, 687, 760, 784, 303 B

[56] References Cited

U.S. PATENT DOCUMENTS

| | | | |
|---|---|---|---|
| 3,070,087 | 12/1962 | Sittel | 128/649 |
| 3,632,305 | 1/1972 | Buchler | 423/242 |
| 3,659,586 | 5/1972 | Johns et al. | 128/635 |
| 3,748,911 | 7/1973 | Rousselet et al. | 73/864.22 |
| 3,763,696 | 10/1973 | Krakau | 128/645 |
| 3,841,310 | 10/1974 | Goldstein | 128/303 B X |
| 3,945,373 | 3/1976 | Tweed et al. | 128/782 |
| 3,973,555 | 8/1976 | Moller et al. | 128/635 |
| 4,182,315 | 1/1980 | Vas et al. | 128/687 |
| 4,207,146 | 6/1980 | Kunke | 204/1 T |

Primary Examiner—Lee S. Cohen
Assistant Examiner—Angela D. Sykes
Attorney, Agent, or Firm—Paul F. McCaul; John R. Manning; Robert D. Marchant

[57] ABSTRACT

An apparatus is described for moving a probe (12) that engages moving living tissue such as a heart or an artery that is penetrated by the probe, which moves the probe in synchronism with the tissue to maintain the probe at a constant location with respect to the tissue. The apparatus includes a servo positioner (18) which moves a servo member (20) to maintain a constant distance from a sensed object (30) while applying very little force to the sensed object, and a follower (26) having a stirrup (28) at one end resting on a surface of the living tissue and another end carrying a sensed object (30) adjacent to the servo member. A probe holder (34) has one end mounted on the servo member (20) and another end which holds the probe (12). The probe is held adjacent to the stirrup (28) of the follower assembly, so that movements of the tissue and therefore of the follower assembly (26) result in corresponding movement of the probe (12) to follow the surface of the tissue.

8 Claims, 3 Drawing Figures

SYSTEM AND METHOD FOR MOVING A PROBE TO FOLLOW MOVEMENTS OF TISSUE

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

Research on living tissue by the application of a probe to the tissue, may be difficult where the tissue must be allowed to move, as in the case of the heart and arteries of an animal. For example, in research an atherosclerosis, measurement and analysis of the oxygenation of arterial walls in living tissue can be accomplished by the insertion of a probe into the tissue. In one procedure, a probe which is small in comparison to cell size, penetrates the tissue in increments of five to ten microns. Since the radial expansion of the arteries is much larger than such increments during a heart beat, meaningful measurements require the probe to maintain a set distance from the arterial wall, within about one micron and with a phase error as close to zero as possible. It would be possible to rest a probe holder directly on the walls of the artery adjacent to the location where the probe penetrates the artery, except that the adjustable probe holder has a considerable mass which would interfere with functioning of the artery if a large portion of the holder mass were to rest on the artery. An apparatus that enabled the probe and a relatively massive probe holder to follow motions of the tissue, while applying minimal loads or other interference to the tissue, would be of considerable value.

SUMMARY OF THE INVENTION

In accordance with one embodiment of the present invention, a method and apparatus are provided for moving a probe to follow the movements of the probed object such as living tissue, while applying minimal force and obstruction to the tissue. An apparatus for moving the probe includes a movable servo member which carries a distance sensor that operates a means for moving the servo member to maintain a constant distance between the servo member and a sensed object. A light weight follower has one end engaged with the tissue so as to be moved by it, and another end forming a sensed object adjacent to the distance sensor, so that the servo member follows movement of the tissue. A probe holder is mounted on the servo member to move with it, and carries a probe which probes the tissue at a location adjacent to the tissue engaging end of the follower. The system therefore locates the distance sensor away from the tissue location being probed, to avoid obstruction of the tissue by the sensor and to avoid any other deleterious effects from the sensor.

The novel features of the invention are set forth with particularity in the appended claims. The invention will best be understood from the following description when read in conjunction with the accompanying drawings.

DESCRIPTION OF THE PREFERRED EMBODIMENTS

Figure 1:
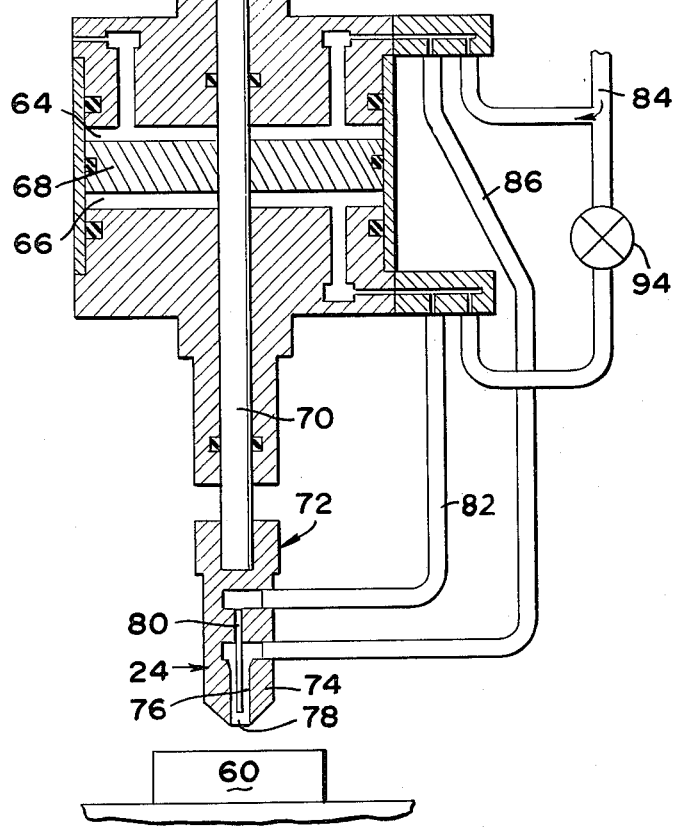
FIG. 1 is a simplified partially elevation and partially perspective view of a probe moving apparatus constructed in accordance with the present invention.

FIG. 1 illustrates an apparatus 10 which is utilized to move a probe 12 which engages living tissue T that is moving, to follow movements of the tissue. In one application wherein research on atherosclerosis is conducted, measurement and analysis of the oxygenation of the walls of an artery are measured by the probe. The probe penetrates the arterial walls in steps of five to ten microns, utilizing a fine needle 14 which is much smaller than the diameter of the cells of the arterial tissue. The system 10 is utilized to move the probe 12 vertically in synchronism with the movement of the upper wall of the artery T which is being penetrated, the pulsations of the arterial walls resulting from pulses of blood flowing therethrough.

The apparatus 10 includes a servo positioner 18 which has a servo member 20 that can move up and down with respect to a frame 22 of the positioner. The servo member 20 carries a proximity or distance sensor 24 fixed in position thereon, which can sense proximity to an object. The servo positioner also includes a mechanism which responds to the sensor 24 to raise and lower the servo member 20 to maintain a constant vertical distance between any point on the servo member 20 and the object sensed by the sensor 24. A follower assembly 25 is provided, which includes a follower 26 that transmits tissue movement to the distance sensor, and a guide 32 that guides the follower in movement along one direction. The follower 26 has a tissue-engaging end forming a saddle 28 for engaging the tissue T, at a location thereof that moves substantially only vertically. The follower also has an opposite sensed end 30 that is positioned close to the distance sensor 24. The guide 32 slidably guides the follower in vertical movement towards and away from the sensor 24. Thus, as the tissue and stirrup 28 move up and down, the sensed object 30 follows such movement, and the movements are detected by the sensor 24 to move the relatively massive servo member 20 up and down. The probe 12 is mounted on a probe holder 34 which is fixed to the movable servo member 20. The probe holder 34 is mounted so that it holds the probe 12 adjacent to the stirrup 28 of the follower. Thus, as the stirrup 28 moves up and down to follow tissue movements, it causes the servo member 20 to follow such movements, and therefore causes the probe 12 to follow the movements. The fine needle 14 which penetrates the tissue, therefore follows movement of the surrounding tissue, to maintain the needle at a constant depth within the tissue. The relatively bulky servo member 20 is spaced away from the probe, and also moves along an axis 19 displaced from the axis 21 along which the stirrup moves.

Figure 2:
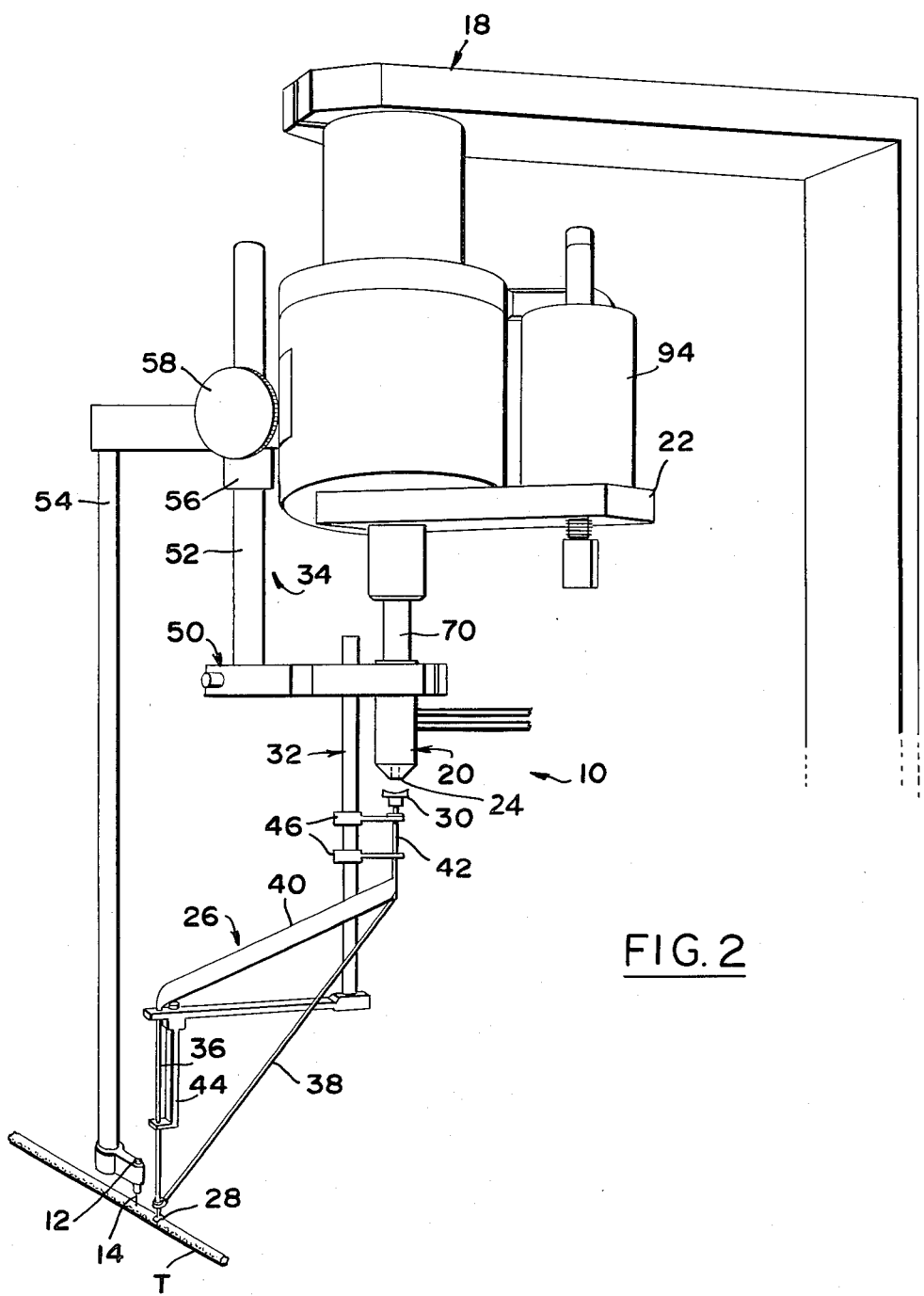
FIG. 2 is a more detailed perspective view of the apparatus of FIG. 1.

FIG. 2 illustrates additional details of the apparatus 10 which moves the probe 12. The follower 26 is constructed to be extremely light in weight by forming it of thin wall tubing and thin sheet materials. In particular, the follower 26 includes a pair of tubes 36, 38 joined together at their lower ends at the stirrup 28 and at their upper ends by a beam 40. Another tube 42 extends vertically to hold the sensed object 30. The guide 32 includes a lower member 44 that guides the follower tube 36 in vertical motion, and an upper pair of members 46 that guide the upper tube 42 of the follower in vertical motion. Since the follower 26 moves only vertically, it can be mounted on a bracket 50 which is fixed to the servo member 20, although it could be instead fixed to the frame 22 of the servo positioner. By mounting the guide on the servo member, the follower 26 need only move a very small distance on the guide, and it would even be possible to mount the follower on the ends of leaf springs held by the guide.

The probe holder 34 includes a first part 52 which is fixed to a bracket 50 that clamps onto the movable servo member 20. A second part 54 of the probe holder is attached to a micro drive attachment 56 of the holder that enables the second member 54 and the probe thereon to be raised and lowered by a controlled minute distance by the turning of a knob 58. The second holder member 54 supports the probe 12 so the needle 14 thereon engages a location on the tissue T which is adjacent to the stirrup 28.

When the location on the tissue engaged by the stirrup 28 moves up or down slightly, the sensed object 30 moves a corresponding distance up or down, and causes the servo member 20 to move a corresponding distance up or down. This causes the probe holder 34 to move a corresponding distance up or down, to thereby move the probe needle 14 to the same extent. The probe needle 14 therefore moves up and down to the same extent as the tissue underlying the stirrup 28. So long as the needle 14 is close enough to the stirrup 28, that the tissue locations engaged by them move substantially in synchronism and by the same amount, the probe needle 14 will follow tissue movement.

Figure 3:
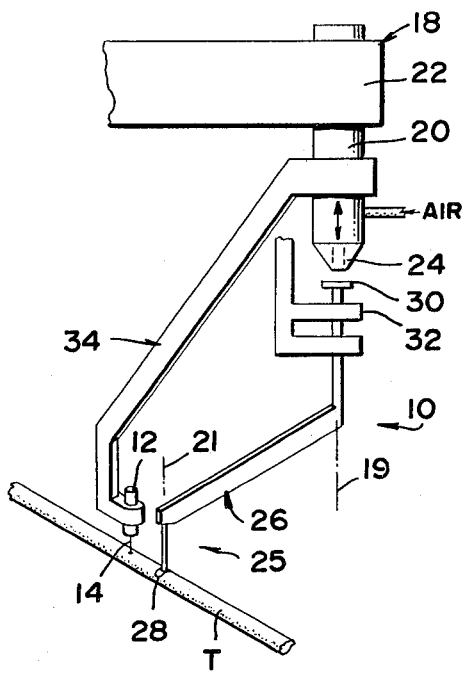
FIG. 3 is a sectional view of a servo that can be utilized in the system of FIG. 1.

The particular servo positioner 18 which has been utilized in the implementation of the invention, is a pneumatic servo manufactured by Schaevitz Engineering, which has been utilized as a non-contacting thickness measuring system for measuring the thickness of metal or other workpieces. FIG. 3 illustrates a simple version of the pneumatic servo positioner showing it being utilized to measure the thickness of an object or work piece 60. Any difference in the air pressures in the 2 chambers 64, 66 of the positioner 62 (less a present difference compensated for by a spring, not shown) causes movement of an actuator plate 68 which is fixed to a piston rod 70 that is part of the servo member 72. A proximity sensor 74 on the servo member includes walls forming a passageway 76 which directs air downwardly out of a sensing orifice 78. Back pressure in the partially enclosed area or chamber formed behind the tip of the orifice 78, is sensed by another tube 80 which is connected through a hose 82 to the control chamber 66. Air under a pressure such as 30 psi is delivered through an input 84 to the reference chamber 64 and through a hose 86 to the passageway 76 to maintain a constant flow of air therethrough.

When the sensing orifice 78 approaches a workpiece 60, the air flow obstructed by the workpiece produces an increased back pressure in the sensing orifice 78 which is transmitted through the tube 80 to the control chamber 66. The increased pressure in the control chamber 66 causes the reference plate 68 to rise until the pressures in the two chambers 64, 68 are equal (or there is a predetermined difference). Thus, the back pressure created by the proximity of the sensing orifice 78 to the workpiece 60, causes the servo member 72 to move up or down so as to maintain a constant distance to the workpiece over a limited range of servo member movements. It may be noted that the system also includes a transformer core 90 fixed to the piston 70 for generating an output on a transformer 92 to enable the generation of a signal indicating changes in servo member position. Also, a valve 94 is provided, which is normally closed, but which can be opened to lift the servo member to its highest position.

The servo positioner 18 shown in FIG. 2, is similar to the pneumatic servo of FIG. 3, except that it also includes a booster 94 that increases the sensitivity of the positioner. In addition, the sensed object 30 is not constructed flat, but instead is constructed with a dished surface to provide a concave face facing the sensing orifice of the proximity sensor 24. The concave surface increases the amount of back pressure produced as the sensor 24 approaches the object 30 to minimize the downward force on the follower. This also permits an object 30 in the form of a slightly concave dish of limited diameter and mass, to be effective in creating a back pressure without having a large diameter. The follower 26 shown in FIG. 2, which was constructed, had a weight of about 2 grams. The servo positioner 18 generated an air pressure force on the sensed object 30 of about 2 grams. Accordingly, the total load on the tissue T was about 4 grams. It would be possible to bias the follower upwardly by perhaps 3 grams to further minimize tissue loading.

The stirrup 28 of the follower assembly was of small dimensions, so that the probe 12 could be placed close to it, and the area immediately around the probe was not obstructed. The follower also was useful in locating the gas-emitting sensor 24 away from the tissue, which is useful because air or other gas blowing directly on the tissue would tend to dry it out. Of course, a variety of mechanisms could be utilized to operate a servo positioner, such as by the use of an object that contacts a sensed object and that moves a core of a voice coil, and with the voice coil being utilized to drive a linear positioner, although the pneumatic servo described herein was found to provide very high precision with an apparatus of relatively moderate cost.

Thus, the invention provides an apparatus and method for moving a probe to follow movements of an object engaged by the probe such as living tissue. The apparatus includes a servo positioner with a movable servo member carrying a distance sensor for measuring changes in the distance to an object. It may be noted that the term proximity or distance sensor relates to a sensor that measures changes in the distance (which may be 0) to an object, and is not limited to a sensor which never touches an object. The apparatus also includes a follower assembly which includes a guide and a follower having one portion engaging the movable tissue and another portion lying adjacent to the proximity or distance sensor, to move the servo member in synchronism with the tissue. A probe holder is mounted on the servo member to move therewith, and carries a probe which is positioned adjacent to the tissue-end of the follower. Accordingly, the probe apparatus which may include a relatively massive probe holder and probe, can be made to move in synchronism with the tissue engaged by the probe, with minimal loading of the tissue and with minimal obstruction of the area immediately around the probe.

Although particular embodiments of the invention have been described and illustrated herein, it is recognized that modifications and variations may readily occur to those skilled in the art and consequently, it is intended that the claims be interpreted to cover such modifications and equivalents .

We claim:

1. Apparatus for use with a probe, to move the probe to follow moving tissue, comprising:
   a servo positioner which includes a frame, a servo member moveably positioned on said frame, a distance sensor means for sensing change of distance to a sensed object and which generates a signal indicating change of distance to said sensed object, said sensor means mounted on said servo member to move with it, and means responsive to said sensor means for moving said servo member to maintain a substantially constant distance from the sensed object;
   a follower assembly which includes a follower having a sensed object near said distance sensor means to be sensed by said sensor means and having a tissue engaging member positioned remote from said sensed object to engage tissue, so that the servo member is directed to follow movements of remotely located tissue, and guide means for guiding movement of said follower toward and away from said sensor means; and
   a probe holder having an inner end mounted on said servo member to move with it, and having an outer end for holding the probe at the tissue.

2. The apparatus described in claim 1 wherein:
   said sensor means emits air from an orifice toward said sensed object, and said means for moving said servo member is responsive to pressure in said orifice; and
   said sensed object has a concave face facing said distance sensor means, to help trap air emitted therefrom to increase the sensitivity of said servo positioner.

3. The apparatus described in claim 1 wherein:
   said servo positioner includes means for normally moving said servo member only along a predetermined axis, said guide means includes means for limiting movement of said follower, said sensed object, and said tissue engaging member thereon in a direction substantially parallel to said axis, and said sensed object is out of the line of movement of said tissue engaging member, whereby said servo member and sensor means can be located to avoid obstruction of the tissue even if not far from it.

4. The apparatus described in claim 1 wherein:
   said tissue engaging member includes a stirrup for lying stably on a surface of the tissue which is associated with by the probe.

5. The apparatus described in claim 1 wherein:
   said guide means includes a guide mounted on said servo member guiding said follower in movement toward and away from said sensor.

6. Apparatus for probing moving tissue comprising:
   a pneumatic servo having a frame, a servo member moveably positioned on said frame and which includes a gas-emitting nozzle, and means responsive to the obstruction of emitted gas from the nozzle by an object in front of the nozzle, for moving the servo member and nozzle thereon relative to said frame, to maintain a constant degree of interruption of emitted gas;
   a follower assembly which includes a tissue engager part for engaging a tissue, a sense object for blocking the free outflow of gas from said nozzle, and a structure connecting said tissue engager part and said sense object;
   guide means for guiding said sense object in movement toward and away from said nozzle; and
   a probe holder mounted on said servo member and having means for holding a probe near said tissue engager part for probing the engaged tissue, to move the probe to follow the tissue without requiring the nozzle to lie closely adjacent to the tissue.

7. The apparatus described in claim 6 wherein:
   said tissue engager part includes a stirrup for lying stably on a surface of the tissue which is probed by the probe.

8. A method for moving a probe that engages living tissue, to follow movements of that tissue, comprising:
   resting a tissue-engaging member of low mass, on a tissue location close to the probe so that the tissue-engaging member moves with the tissue portion engaged by the probe;
   sensing movements of said tissue-engaging member and moving a servo member to follow movements of said tissue-engaging member; and
   mounting a probe holder that holds said probe, on said servo member, so that the probe can follow movements of said tissue.

* * * * *